United States Patent [19]

Newman et al.

[11] 4,223,093
[45] Sep. 16, 1980

[54] CULTURE COLLECTION AND TRANSPORT DEVICE

[75] Inventors: Howard F. Newman, Los Angeles; David L. King, Valencia, both of Calif.

[73] Assignee: Precision Dynamics Corporation, Burbank, Calif.

[21] Appl. No.: 935,841

[22] Filed: Aug. 25, 1978

[51] Int. Cl.² ............................................. C12M 1/30
[52] U.S. Cl. .................................. 435/295; 128/759; 435/294; 435/810; 435/296; 435/300
[58] Field of Search ............... 195/127, 139; 128/638, 128/743, 759; 435/292, 293, 294, 295, 810, 296, 299, 300

[56] References Cited

U.S. PATENT DOCUMENTS

| 3,163,160 | 12/1964 | Cohen | 195/139 |
|---|---|---|---|
| 3,450,129 | 6/1969 | Avery et al. | 128/759 |
| 3,513,830 | 5/1970 | Kalayjian | 128/759 |
| 3,835,834 | 9/1974 | Brown et al. | 128/759 |
| 3,876,503 | 4/1975 | Mennen | 195/127 X |
| 3,915,806 | 10/1975 | Horlach | 195/127 X |
| 3,966,552 | 6/1976 | Pagano et al. | 195/139 |
| 4,014,746 | 3/1977 | Greenspan | 195/139 X |
| 4,018,653 | 4/1977 | Mennen | 195/127 |

Primary Examiner—Robert J. Warden
Attorney, Agent, or Firm—Mahoney & Schick

[57] ABSTRACT

A culture collection and transport device which is uniquely configured employing a piston-like element which is adapted to maintain a medium-carrying chamber in fluid-tight relationship until such time as a specimen sample is introduced into the device and selectively put in contact with the medium. The culture medium preserves the viability of microorganisms comprising the specimen sample. The piston-like member is pressure responsive so that ambient temperature and pressure changes will not cause leakage of the medium from the medium-carrying chamber and wherein a simple, force oriented movement of a specimen collector on swab, containing a culture, is readily put into contact with the viability-maintaining, transport medium.

16 Claims, 9 Drawing Figures

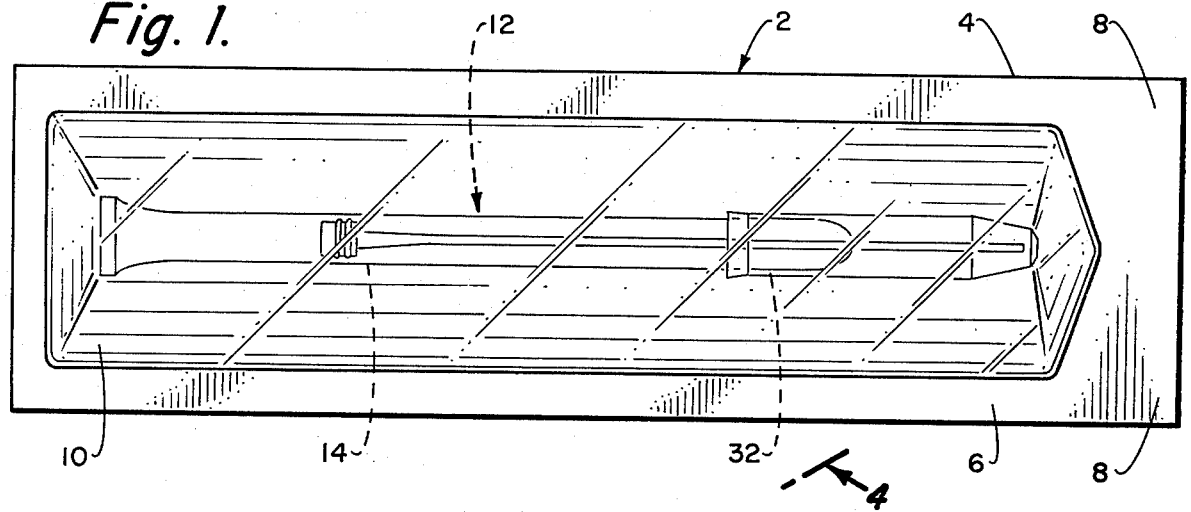
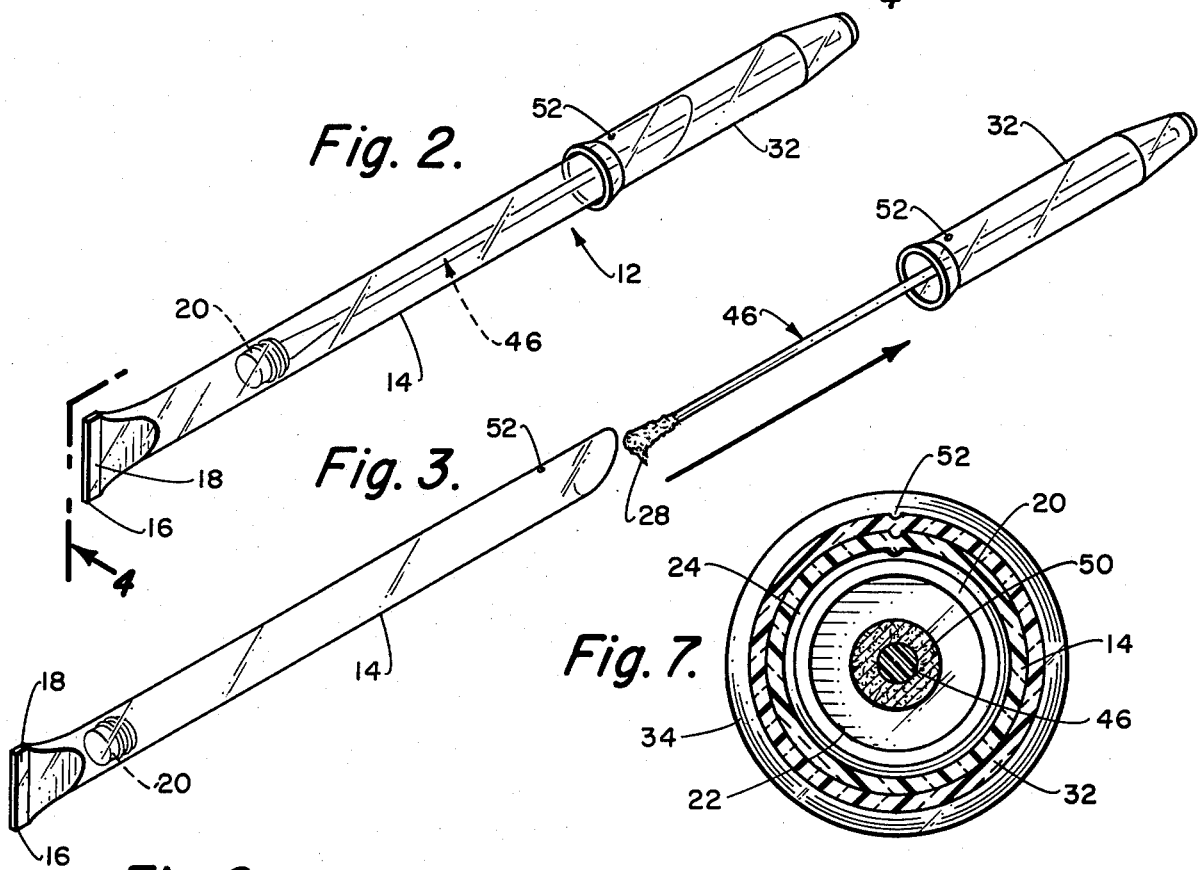
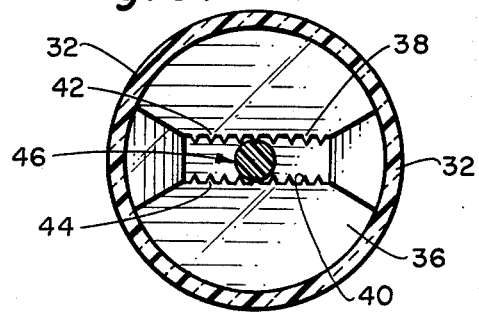
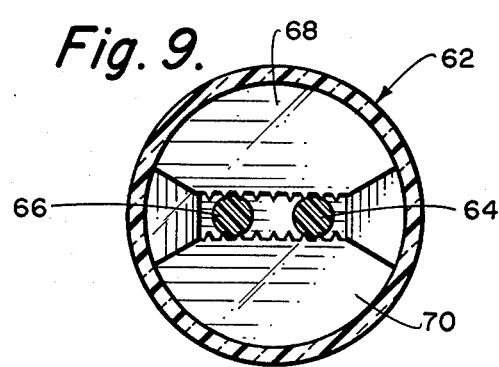

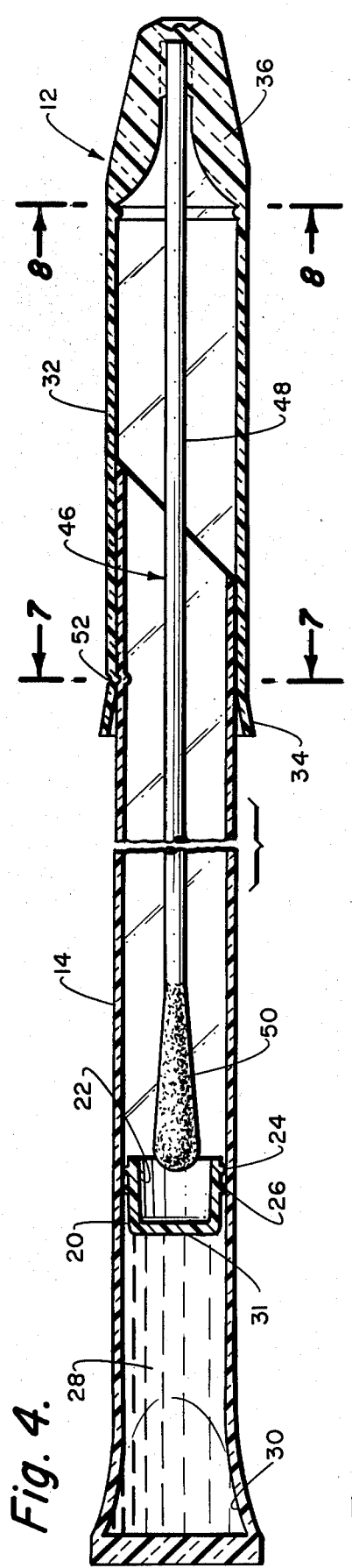
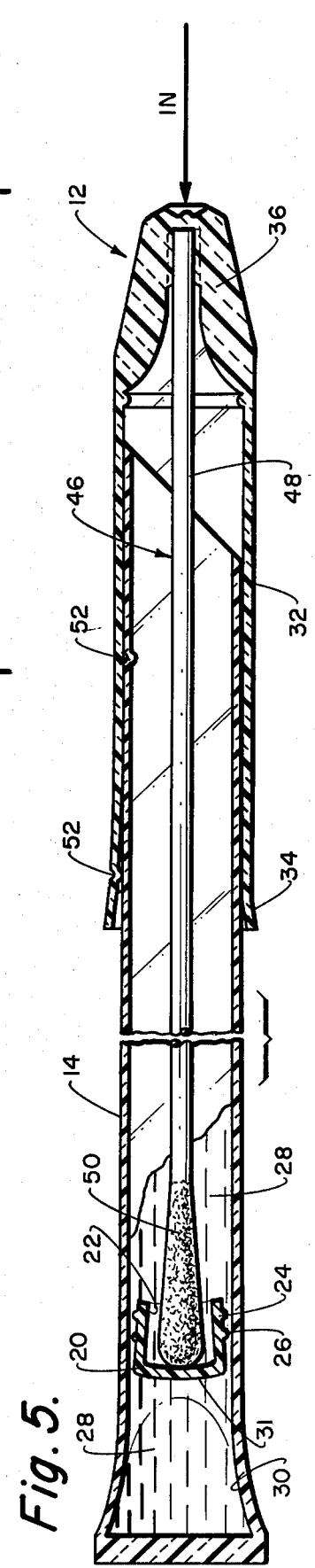
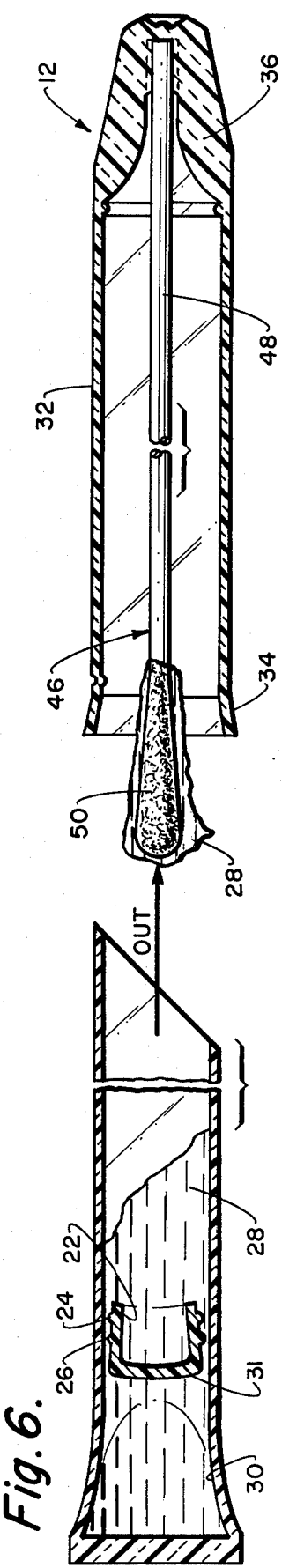

CULTURE COLLECTION AND TRANSPORT DEVICE

BACKGROUND OF THE INVENTION

This invention pertains to culture collection and transport devices of the type utilized in doctors' offices and the like wherein a specimen is obtained from a patient. In order to maintain the viability of the microorganism obtained as a specimen, until such time as the specimen can be tested by a testing laboratory, the microorganism must be maintained, and must be put in contact with a culture-sustaining medium, such as Amies, agar or other media that will preserve the viability of microorganisms for in vitro diagnostic test purposes.

In taking a culture specimen, a culture collection and transport device must be such that sterility of the specimen collector, e.g. swab, is maintained in a sterile environment and can be handled in an aseptic manner after the specimen of the microorganisms has been taken. Thereafter, the culture collection and transport device must be capable of furnishing a life-sustaining medium for the specimen microorganisms so that their viability will be maintained until such time as adequate laboratory tests may be made. Thus, a culture collection and transport device must be sterile before a test specimen is introduced, must have a microorganism-sustaining fluid or medium for the transportational phase and, subsequent to the specimen taking, must be capable of maintaining specimen integrity so as to give accurate test results. Additionally, because millions of cultures are taken annually, the devices must be economically and feasibly manufactured and must be of relative low cost because of their single-use character.

Prior art devices have utilized glass ampuls, partial and rupturable seals to maintain a culture-sustaining medium in isolation from the specimen collector, usually a swab or the like, until such time as the specimen of microorganisms has been obtained. The prior art devices suffer in that they are difficult to manufacture and to maintain quality control over, are costly in the manufacture of the various components making up the culture collection and transport device and generally suffer from other shortcomings, which the devices of this invention overcome.

OBJECTS AND SUMMARY OF THE INVENTION

It is an object of the invention to provide a culture collection and transport device which is suitable for in vitro diagnostic use.

It is another further object of the invention to provide a culture collection and transport device which employs a sealing member which is responsive to ambient pressure so as to prevent leakage of microorganism-maintaining medium.

It is still a further, and even more important, object of the invention to provide a culture collection and transport device which employs a piston-like member of unique configuration which maintains a culture medium chamber in fluid-tight relationship until such time as it is desired to disrupt that relationship.

It is still an even further, and more specific, object of the invention to provide a culture collection and transport device using an open-ended, tubular-like body member having a closed end which is adapted to carry a culture medium in one end thereof which is sealed off from the remainder of the tubular-like body member by means of a piston-like member which is responsive to ambient pressure.

It is still another, even more specific and important, object of the invention to provide a culture collection and transport device which employs a piston-like member of conformable material wherein the piston-like member may provide a fluid-tight barrier between a body of culture medium and a specimen collector.

It is still another further, even more specific and important, object of the invention to provide a culture collection and transport device employing a cap-swab subassembly and a tube subassembly wherein the tube subassembly carries a culture medium maintained in a normally fluid-tight chamber by means of a piston-like, conformable member which is responsive to ambient pressure and which is selectively disengageable in order to provide culture medium contact with the specimen collector as desired.

It is still another, even more specific, and further object of the invention to provide a culture collection and transport device which employs two plastic tube members, one of which carries a culture medium separated from the remainder of the tube by a piston-like sealing member, and wherein the other tubular member carries a specimen collector such as a swab and wherein the two tubes fit together to form a single unitary aseptic culture taking and transport device.

It is another, even more further specific, object of the invention to provide a culture collection and transport device using a piston-like member which is of conformable material employing at least one perimetric sealing surface, protuberance or lip thereabout so as to provide a fluid-tight chamber for a culture medium carried in the device.

It is still a more further, and even more specific, object of the invention to provide a culture collection and transport device utilizing a piston-like member, employing perimetric sealing surfaces, protuberances or lips thereabout, which is of a unique configuration and design so as to be responsive to ambient pressure and to selectively permit collapse upon itself to disrupt the fluid-sealing character thereof.

In one embodiment, the invention pertains to a culture collection and transport device comprising the combination of an open-ended, tubular-like body member or tube subassembly having a closed end adapted to carry a fluid thereat and employing a conformable, piston-like member slideably positionable adjacent the closed end to form a normally, fluid-tight, chamber therebetween, in which a fluid medium is carried. The piston-like member has a least one perimetric, continuous, sealing surface, protuberance or lip thereabout in abutting relationship to the interior surface of said tubular-like body or tube subassembly member. The piston-like member is partially collapsible when subjected to selected applied pressure to open a fluid passage thereabout. A cap assembly member having disposed therein one or more specimen collectors and of a sufficient size to telescopically receive the open-ended, tubular-like body or tube subassembly member completes the major components of the culture collection and transport device.

These and further objects of the invention will become apparent from the hereinafter following commentary taken in conjunction with the figures of drawing.

BRIEF DESCRIPTION OF THE DRAWING

FIG. 1 is an elevational view showing the culture collection and transport device of the invention in an aseptic package;

FIG. 2 is a perspective view of the culture collection and transport device illustrated in FIG. 1, but being shown outside of the package in which it would normally be carried;

FIG. 3 is a view similar to FIG. 2 illustrating the major components making up the culture collection and transport device of the invention;

FIG. 4 is a view taken along the line 4—4 of FIG. 2;

FIG. 5 is a view similar to FIG. 4, but illustrating the mode of contacting the specimen collector with the culture medium carried by the culture collection and transport device of this invention;

FIG. 6 is a view similar to FIG. 5, but illustrating the culture medium and microorganisms retained on the tip of a specimen collector;

FIG. 7 is an enlarged view taken along the line 7—7 of FIG. 4;

FIG. 8 is an enlarged view taken along the line 8—8 of FIG. 4; and

FIG. 9 illustrates a section view of an alternative embodiment of the invention wherein the cap subassembly member carries more than one specimen collector or swab.

DESCRIPTION OF THE BEST EMBODIMENTS CONTEMPLATED

Referring to the drawings, wherein like numerals of reference designate like elements throughout, it will be seen that a package 2 contains a first paper sheet 4, heat or adhesively sealed to plastic over sheet 6 except at the corners 8 for ease of opening purposes, thereby forming a sterile chamber 10 in which is disposed the culture collection and transport device 12 of this invention.

The culture collection and transport device 12 comprises a first open-ended, tubular-like body member or tube subassembly 14 sealed at one extremity 16, leaving surface 18 to which may be affixed by heat stamp, imprinting or other means a lot number or identification to enable traceability throughout the life of culture collection and transport device 12. The open end of the member 14 is beveled for ease of association with a cap member as will be seen hereinafter. Also, ideally the tube diameter is sufficiently large to permit ease of access and egress of a specimen collector without wiping the specimen from the collector, as will be readily apparent.

Disposed in spaced relationship from the end 16 is piston-like member 20, which may be of natural or synthetic rubber or of one of the plastics, such as Krayton, a trademarked product of the Shell Company, or Polyurethane. The piston-like member 20 may be compression molded or injection molded and, depending upon the materials of construction, will be soft and conformable and have some lubricity, either by way of the materials of construction themselves or will utilize silicone oil or the like applied after fabrication or added to the materials making up the member 20 for purposes that will become apparent.

Piston-like member 20, in this particular instance, is of cup-like design having an interior recess 22 with spaced sealing lips or protuberances 24 and 26 about the perimeter of the outer wall of piston-like member 20. The piston-like member 20 is conformable and, generally, will have a shore A rating in the 40–70 range for the size of piston-like member 20 utilized in the type of culture collection and transport device 12 illustrated in the figures of drawing. Thus, for general use purposes, a piston-like member 20 as illustrated will have a wall thickness of about 0.035 inches and a diameter of approximately 0.453 inches, it being understood that the length of the tube subassembly 14 being approximately 6.19 inches. It is only important that piston-like member 20 be capable of forming a fluid-tight barrier, as will be described, and be capable of being responsive to ambient pressures to which the culture collection and transport device 12 will be subjected. Further, as will be seen, the piston-like member 20 should be collapsible upon itself and be operative for its apparent purposes within an operating range of between 2–4 pounds or thereabout for the particular device being described, and it should be understood that those of ordinary skill in the art will understand the various modifications and changes that would necessarily be inherent should larger or smaller devices be desired, keeping in mind the foregoing parameters.

Positioned adjacent the closed end 16 of tubular-like body member or tube subassembly 14 is a quantity of culture medium 28 which may be Amies clear or charcoal, agar or any other type of generally suitable microorganism sustaining media well known in the art. Generally speaking, the fluid level of the culture medium 28 will be somewhat less than that amount that can be retained within the culture medium chamber 30 formed between the lower end 16 of tube subassembly member 14 and the bottom wall 31 of piston-like member 20 so that a quantity of air (not shown) will provide an air spring to cushion impact or shock loads on the medium chamber 30 due to ambient pressure, so that the piston-like member 20 may slide within the interior of tube subassembly 14 and still maintain the fluid-tight barrier between medium chamber 30 and the remainder of tube subassembly member 14.

Referring to FIG. 4, it will be seen that the piston-like member 20, by means of spaced sealing surfaces or lips 24 and 26, provides a fluid barrier to maintain substantial fluid integrity within medium chamber 30. The cap assembly member 32 is also of tubular configuration, having a slightly larger inside diameter so as to be telescopically received over the upper end portion of tube subassembly member 14. For ease of telescopic association, cap assembly member 32 has a flared end 34 and a closed end 36, molded in the interior surface to form opposed interior gripping surfaces 38 and 40 (FIG. 8) having spaced serrated projections 42 and 44 in which is frictionally retained a specimen collector or swab 46, the shaft 48 being made of plastic or the like with the tip 50 being of rayon absorptive material of the type generally found in the culture collection field.

Referring to FIG. 4, it will be noted that the overall length of specimen collector or swab 46 is such that room is left between the inside recess surface 22 (more particularly, the inside, bottom wall of piston-like member 20) and the outer periphery of rayon tip 50 of swab 46. Thus, as seen in FIG. 4, the piston-like member 42 may linearly move between the closed end 16 and the open end of tube subassembly member 14, due to the influence of ambient pressures acting upon the fluid medium 28 or air contained within fluid medium chamber 30. Because of the sealing protuberances or lips 24 and 26 and the coaction of the configuration of piston-like member 20 and the lubricity of the materials of construction of both the piston-like member 20 and the tube subassembly 14, a fluid barrier or fluid tightness is achieved to prevent any contact of the fluid medium 28 with swab tip 50, except under desired and selected circumstances, as will be described.

In the FIG. 4 showing, the cap assembly member 32 is shown as being heat sealed or tack welded, as at 52, so as to join cap assembly member 32 to tube subassembly member 14 in releasable fashion. Thus, by simply twisting the cap assembly member 32 the tack weld or tamper indicator 52 seal will be broken to allow removal of the cap assembly 32 with its captively retained or staked swab 46, so that a microorganism specimen may be taken by means of swab tip 50.

Referring to FIG. 5, once the specimen has been collected, it is now imperative, for transportational purposes and to maintain the viability of the microorganism specimen, that the fluid medium be put into association with the tip 50. Thus, once the specimen is taken, the user of the culture collection and transport device would merely position the cap assembly member 32 with specimen collector 46, as illustrated in FIG. 2, and by means of using one hand and having the thumb in ballpoint pen actuating position, depress the outer end 36 of cap assembly member 32 in the direction of the arrow illustrated in FIG. 5 to thereby drive the tip 50, having the specimen thereon, into abutting engagement with the interior recess 22 of piston-like member 20, which because of the noncompressibility of the fluid medium 28 in fluid chamber 30 will cause the walls of piston-like member 20 to collapse about itself to thereby break the perimetric seals formed by sealing surfaces or members 24 and 26 to provide fluid paths for medium 28 to flow thereabout and contact the microorganisms contained on swab tip 50.

Referring to FIG. 6, obviously in order to remove the specimen and to make whatever microorganism test would be desirable, the cap assembly member 32 is removed, containing on the swab tip 50 not only the collected specimen in viable form, but a portion of the fluid medium 28 which has saturated the swab tip 50 in order to maintain and to preserve the viability of the collected specimen for in vitro testing purposes.

Referring now to FIG. 9, an alternative type of cap assembly 62 is illustrated identical in all particulars to cap assembly member 32 except, in this particular instance, two specimen collectors or swab members 64 and 66 are carried in frictionally retained relationship between the interior of sidewalls 68 and 70 making up the upper end of cap assembly 62. In all other particulars, the serrated interior surfaces of wall members 68 and 70 serve to frictionally retain the plastic shafts of swab members 64 and 66. Thus, with the dual concept, two specimen collectors are provided for specimen collection purposes.

In the specimen collection and transportational device 12 illustrated, it should be remembered that the specific description is for illustrative purposes only. For example, while the tube subassembly member 14 and the cap assembly member 32 are made of polyethylene, other materials of construction are, indeed, possible, keeping in mind the sliding parameter that is necessary for the piston-like member 20 with respect to the interior wall of the tube subassembly member 14. In some instances, the microorganism-sustaining fluid will be of varying colors and the piston-like member 20 may likewise be colored to accommodate the specific color of the medium with which it is to be used.

The piston-like member must have sufficient sealing integrity so as to be able to provide the fluid barrier between the culture media chamber and the remainder of the tube subassembly and, thus, the parameters of the material of construction of both the piston-like member, the tube subassembly and the relative sizes of each must be coordinated so that the forces that may cause bending of the swab shaft would be greater than the force necessary to break the fluid barrier maintained by the piston-like element, which, in turn, would be greater than the static friction force between the interior of the tube subassembly member and the conformable or elastomeric piston-like member.

The piston-like member and the interior wall of said tubular-like body member have relative coefficients of friction so as to permit said piston-like member to be responsive to fluid pressure changes in said normally fluid-tight chamber while maintaining fluid sealability about said piston-like member through said sealing lips. Thus, as indicated hereinbefore, the various component factors should provide an overall device that will only require between 2 and 4 pounds of force in order to break the fluid barrier formed by piston-like member 20 and still attain the aforealluded to advantages.

The culture collection and specimen device of the invention, of course, may be utilized without an outer package. An outer package like that illustrated is however, deemed necessary where exterior sterility of the culture collection and specimen device is desired. Additionally, in some instances, a cap assembly having the retained swab may be dispensed with and other alternative means utilized in order to obtain the specimen, in which event only the tube subassembly member need be utilized. Various changes and modifications will make themselves apparent to those of ordinary skill in the art, and all such changes will not depart from the essence of the invention as disclosed herein and as intended to be covered in the appended claims.

We claim:

1. A culture collection and transportational device comprising the combination of: an open-ended, tubular-like body member having a closed end adapted to carry a fluid thereat; a conformable piston-like member slideably positionable adjacent said closed end to form a normally fluid-tight chamber therebetween in which said fluid medium is carried, said piston-like member having at least one perimetric continuous sealing lip thereabout in abutting relationship to the interior surface of said tubular-like body member, said piston-like member being partially collapsible when subjected to selected applied pressure to open a fluid passageway about the outer periphery of said piston-like member.

2. The device in accordance with claim 1 including a cap member adapted for telescopic association with said tubular-like body member.

3. The device in accordance with claim 2 wherein said cap member includes a specimen collector releasably carried thereby.

4. The device in accordance with claim 1 wherein said piston-like member is collapsible upon itself and has two spaced continuous sealing lips about the perimeter thereof, each of which is in abutting relationship to the interior surface of said tubular-like body member.

5. A device in accordance with claim 4 wherein a cap member is telescopically received on the open end of said tubular-like body member and one extremity thereof is adapted to receive the shaft of a specimen collector in releasably, frictionally-held association therewith.

6. The device in accordance with claim 5 wherein said piston-like member is cup-shaped, wherein an open recess surface is projected to and positioned adjacent at the specimen end of said specimen collector.

7. The device in accordance with claim 6 wherein said piston-like member is made of conformable material having elastomeric characteristics.

8. The device in accordance with claim 7 wherein said piston-like member and the interior wall of said tubular-like body member have relative coefficients of friction so as to permit said piston-like member to be responsive to fluid pressure changes in said normally fluid-tight chamber while maintaining fluid sealability about said piston-like member through said sealing lips.

9. The device in accordance with claim 8 including a quantity of culture medium disposed in said fluid-tight chamber and a gaseous space between the surface of said medium and the presented surface of said piston-like member, whereby an air cushion or spring is provided for absorption of relatively high impact forces so as to maintain fluid sealability of said piston-like member, and wherein fluid sealability is disrupted of said piston-like member by impacting the recessed end of said piston-like member with said specimen collector.

10. The device in accordance with claim 6 wherein said cap member is adapted to receive two specimen collectors in friction held, side-by-side relationship and said cap member telescopically receives the exterior, circumferential surface of said tubular-like body member.

11. The device in accordance with claim 6 wherein said tubular-like body member and said cap member are of heat-sealable plastic and wherein a tack weld is provided between said cap member and said tubular-like body member so as to provide a tamper evident seal.

12. A culture collection and transport device comprising the combination of: an open-ended plastic tubular body member having a sealed end; a conformable, piston-like member slideably positioned from said sealed end and forming a fluid-tight chamber therebetween, a quantity of fluid carried in said fluid-tight chamber, said piston-like member having spaced sealing surfaces coacting with the interior wall of said open-ended, plastic tubular body member to selectively maintain the fluid tightness of said fluid-tight chamber and being pressure responsive to disrupt said sealing surfaces upon the application of a selected fluid pressure within said fluid-tight chamber.

13. The culture collection and transport device in accordance with claim 12 including a plastic cap member carrying a swab and telescopically received over the upper end portion of the open end of said open-ended, plastic tubular body member to thereby cooperatively form an elongated, closed chamber.

14. The culture collection and transport device in accordance with claim 13 when said piston-like element is of relatively thin-wall, elastomeric-like material of construction, and has a recessed or cup-like surface adjacent the tip of said swab.

15. The culture collection and transport device in accordance with claim 14 wherein said spaced sealing surfaces are formed by spaced, continuous protuberances on the exterior surface of said piston-like member.

16. A culture collection and transport device comprising the combination of: an open-ended plastic tubular body member having a sealed end; a conformable, piston-like member slideably positioned from said sealed end and forming a fluid-tight chamber therebetween, a quantity of fluid carried in said fluid-tight chamber, said piston-like member having spaced sealing surfaces coacting with the interior wall of said open-ended, plastic tubular body member to selectively maintain the fluid tightness of said fluid-tight chamber and being pressure responsive to disrupt said sealing surfaces upon the application of a selected fluid pressure within said fluid-tight chamber, and a plastic member carrying a swab and being telescopically received over the upper end portion of the open end of said open-ended, plastic tubular body member to thereby cooperatively form an elongated, closed chamber.

* * * * *